United States Patent
Verstege et al.

(10) Patent No.: US 9,810,528 B2
(45) Date of Patent: Nov. 7, 2017

(54) OPTICAL SHAPE SENSING WITH A PLURALITY OF OPTICAL FIBERS

(71) Applicant: KONINKLIJKE PHILIPS N.V., Eindhoven (NL)

(72) Inventors: Marco Verstege, Eindhoven (NL); Sander Hans Denissen, Best (NL); Bharat Ramachandran, Morganville, NJ (US)

(73) Assignee: Koninklijke Philips N.V., Eindhoven (NL)

( * ) Notice: Subject to any disclaimer, the term of this patent is extended or adjusted under 35 U.S.C. 154(b) by 132 days.

(21) Appl. No.: 14/895,275

(22) PCT Filed: Jun. 27, 2014

(86) PCT No.: PCT/EP2014/063659
§ 371 (c)(1),
(2) Date: Dec. 2, 2015

(87) PCT Pub. No.: WO2014/207182
PCT Pub. Date: Dec. 31, 2014

(65) Prior Publication Data
US 2016/0102969 A1    Apr. 14, 2016

Related U.S. Application Data

(60) Provisional application No. 61/840,956, filed on Jun. 28, 2013.

(30) Foreign Application Priority Data

Jul. 19, 2013 (EP) .................................... 13177245

(51) Int. Cl.
*G01B 11/24* (2006.01)
*G01B 11/16* (2006.01)
(Continued)

(52) U.S. Cl.
CPC .............. *G01B 11/24* (2013.01); *A61B 34/20* (2016.02); *A61B 90/361* (2016.02); *G01B 11/18* (2013.01); *A61B 2034/2061* (2016.02)

(58) Field of Classification Search
CPC ......... G01B 11/24; G01B 11/18; A61B 34/20; A61B 90/361; A61B 2034/2061
(Continued)

(56) References Cited

U.S. PATENT DOCUMENTS 8,358,883 B2    1/2013    Prisco
2008/0004634 A1    1/2008    Farritor et al.
(Continued)

FOREIGN PATENT DOCUMENTS

TW    M1356513 U    5/2009
WO    201115873 A2    2/2011
(Continued)

*Primary Examiner* — Seung C Sohn

(57) ABSTRACT

An optical shape sensing system and method with at least two optical fibers (OSF1, OSF2) both comprising optical shape sensing elements. A processor (P) is arranged to register a coordinate system indicative of a position of one of the optical fibers (OSF1) in space, and to register a position (R2) of the other optical fiber (OSF2) in relation to this coordinate system. An optical console system (C, C1, C2) serves to interrogate the optical shape sensing elements in both optical fibers (OSF1, OSF2), and to accordingly determine a measure of a three-dimensional shape (I) of both optical fibers (OSF1, OSF2), based on the registered position (R2) of the second optical fiber (OSF2) in relation to the coordinate system. This provide the possibility of providing 3D optical shape sensing of the length of both optical fibers (OSF1, OSF2), thus allowing 3D shape reconstruction of e.g. long medical devices with lengths of several meters. More than two shape sensing optical fibers, e.g. incorporated in separate devices, can be registered in this manner in a
(Continued)

hierarchical data structure, thus allowing shape sensing of very long instruments.

12 Claims, 3 Drawing Sheets

(51) Int. Cl.
    *A61B 34/20* (2016.01)
    *A61B 90/00* (2016.01)

(58) Field of Classification Search
    USPC .............................. 250/559.21, 206; 385/12
    See application file for complete search history.

(56) References Cited

U.S. PATENT DOCUMENTS

| | | | |
|---|---|---|---|
| 2008/0071143 A1 | 3/2008 | Gattani et al. | |
| 2008/0212082 A1* | 9/2008 | Froggatt | G01M 11/083 356/73.1 |
| 2008/0285909 A1* | 11/2008 | Younge | A61B 5/1076 385/13 |
| 2011/0098533 A1 | 4/2011 | Onoda et al. | |

FOREIGN PATENT DOCUMENTS

| | | | |
|---|---|---|---|
| WO | 2011158273 A2 | 12/2011 | |
| WO | 2012168855 A1 | 12/2012 | |

* cited by examiner

OPTICAL SHAPE SENSING WITH A PLURALITY OF OPTICAL FIBERS

CROSS-REFERENCE TO PRIOR APPLICATIONS

This application is the U.S. National Phase application under 35 U.S.C. §371 of International Application Serial No. PCT/EP2014/063659, filed on Jun. 27, 2014, which claims the benefit of U.S. Application Ser. No. 61/840,956, filed on Jun. 28, 2013 and European Patent Number 13177245.1 filed on Jul. 19, 2013. These applications are hereby incorporated by reference herein.

FIELD OF THE INVENTION

The present invention relates to the field of shape sensing, especially three-dimensional (3D) optical shape sensing.

BACKGROUND OF THE INVENTION

By using optical shape sensing, the shape of an elongated object, e.g. a steerable medical device, can be reconstructed by integration of an optical fiber with optical shape sensing elements in such a device. This is possible by optical interrogating the optical fiber e.g. with optical shape sensing elements by means of Fiber Bragg Gratings or Rayleigh based elements. A real time visualization of the reconstructed 3D shape has a number of applications, e.g. medical applications, since it allows important navigational guidance for elongated interventional medical devices. Such devices can be used for example within medical applications in the form of diagnostic and navigation devices, e.g. catheters, guide wires, endoscopes, stylets or needles, and treatment devices, e.g. ablation devices.

In practical implementations, optical shape sensing is possible with an acceptable degree of accuracy up to a length of 1.5-2 meters. However, the optical fiber itself can be several meters long. For some applications, this length limitation is undesired. This limitation can be mitigated by using two separate optical shape sensing devices being tracked with respect to their position in one X-ray image. However, this is unpractical since it requires extra work, and accuracy may be compromised. Further, for some applications such two optical shape sensing devices can be too far apart for such method to work.

WO 2012/168855 A1 discloses a system for monitoring changes during therapy and includes first and second probing segments with optical fiber sensor disposed therein. The second segment is generally disposed apart from the first probe and provides a spatial reference point for the first segment. The first and second segments have at least one common position to function as a reference between the first and second probes.

US 2011/0098533 A1 discloses a medical instrument including a distortion probe disposed in an insertion portion to be inserted into the interior of an examinee provided with a plurality of FBG sensor sections that detect distortion of the insertion portion, and a coordinate calculation section that calculates first three-dimensional coordinates of the respective FBG sensor sections according to a first three-dimensional coordinate system.

SUMMARY OF THE INVENTION

It would be advantageous to provide a method and an optical shape sensing system capable of providing a high precision 3D optical shape sensing over a length exceeding what is possible with a single optical fiber.

In a first aspect, the invention provides an optical shape sensing system as defined by appended claim 1.

Such system is advantageous for incorporation into e.g. one elongated medical devices or other long elongated objects which are desirable to track with respect to 3D shape at a high precision. The invention is based on the insight that two or more optical shape sensing fibers can be mechanically concatenated to provide 3D shape sensing of a long object, since position data of the second optical fiber are registered in relation to the first coordinate system, e.g. with this coordinate system defined by e.g. the position and orientation of the origin (proximal end) of the first optical fiber. The sensing of the position of the second optical fiber, e.g. the origin (proximal end) of the second optical fiber, can be defined relative to a position of the tip (distal end) of the first optical fiber. There are several ways to perform the sensing of position data for the second optical fiber in the first coordinate system, as will be appreciated in the description of embodiments in the following.

By 'coordinate system' is understood any data representation allowing a unique identification of a three-dimensional position. With the phrase 'first coordinate system indicative of a position of the first optical fiber in space' is meant that the coordinate system moves along with the first optical fiber, thus moving or changing orientation of a reference point of the first optical fiber selected to define the origin of the coordinate system will thus change the coordinate system in 3D space.

It is to be understood that the second optical fiber can be directly fixed to the first optical fiber. However, the second optical fiber can also be connected to a near distal point or near distal point of the first optical fiber via a rigid object of known shape, e.g. two fixed positions on a table, or via one or more non-rigid or rigid object(s), as long the relative positions of the first and second optical fibers is known.

The processor may be arranged to register both a position in space and an orientation of a proximal part of the second optical fiber in relation to the first coordinate system. Thus, in this way, the second optical fiber serves to extend the effective length of the first optical fiber, thus allowing optical shape sensing over a longer distance.

The optical console system may comprise a first optical console arranged for interrogating the optical shape sensing elements in the first optical fiber, and a second optical console arranged for interrogating the optical shape sensing elements in the second optical fiber. Especially, such separate optical consoles for each optical fiber may form part of separate devices, thus the system allows separate devices with optical shape sensing capabilities to be registered relative to the first coordinate system, hereby allowing such separated devices to cooperate to produce one combined 3D shape sensing visualization.

An image detector may be arranged at or near a distal part of the first optical fiber, and wherein the image detector is arranged to detect a measure of the position of the second optical fiber. Especially, such image detector may comprise: a visible light camera, an ultrasound sensor, a radio frequency sensor, or an X-ray device. E.g. with a camera placed near a tip (distal end) of the first optical fiber, it is possible to link this position in space of the first optical fiber with a part of the second optical fiber, provided the camera can detect a part of the second optical fiber. Image processing techniques may be applied to process an output from the camera to arrive at a 3D position, e.g. of an origin (proximal end), of the second optical fiber.

A distal part of the first optical fiber may be mechanically arranged adjacent to a proximal part of the second optical fiber, so as to form an overlapping curve between the first and second optical fibers, and wherein the optical console system is arranged to generate a measure of three-dimensional shape of at least part of said overlapping curve between the first and second optical fibers. Thus, with a distal end of the first optical fiber overlapping with a proximal end of the second optical fiber, a reliable measure of spatial position of the second optical fiber relative to the selected first coordinate system can be obtained, thereby ensuring a high accuracy, even in embodiments with even more optical fibers constituting one long shape sensing chain. Especially, the optical shape sensing system may be arranged to correct a three-dimensional shape reconstruction of the first optical fiber in response to the measure of three-dimensional shape of said at least part of said overlapping curve between the first and second optical fibers. With the first and second optical fibers thus being stitched together over a limited longitudinal portion of their extension, there are possibilities to have overlapping shape sensing data which can be used to improve the shape reconstruction of the distal end part of the first optical fiber. This may in some cases be used to ensure that a longer part of an optical shape sensing fiber can be utilized without compromising accuracy in shape reconstruction of the distal part of the fiber.

The optical shape sensing system may comprise an auxiliary object, and wherein the processor is arranged to register a position of the auxiliary object in relation to the first coordinate system in a hierarchical data structure. Especially, the system may comprise a plurality of auxiliary objects, wherein the processor is arranged to register position of the plurality of auxiliary object in relation to the first coordinate system in a hierarchical data structure, wherein at least one of the plurality of objects is linked to position data registered for at least two objects higher up in the hierarchical data structure. Such auxiliary object or objects may or may not contain optical fibers arranged for optical shape sensing. E.g. an object may be a table or the like, to which another object, e.g. an optical shape sensing device is attached. This will allow a chain of several objects to form the basis for a registration of position data of the objects that will allow a correct tracking of position and orientation of a very distally positioned optical shape sensing device relative to the first coordinate system, even though there are several intermediately located objects. Especially, at least one of the plurality of auxiliary object may comprise a third optical fiber with optical shape sensing elements, and wherein the optical shape sensing system is arranged to correct a three-dimensional shape reconstruction of the third optical fiber in response to data registered higher up in the hierarchical data structure than where position data for the third optical fiber is registered. By 'third optical fiber' is here merely understood at least one optical fiber apart from the first and second optical fibers already defined above. Since each auxiliary object is linked to at least two objects higher up in the hierarchical data structure, it is possible to verify or correct any inconsistency in position data registered for a given object, and it is even possible to completely skip one object in a chain of objects for use in shape reconstruction, if its shape sensing complete fails or if the position registered for such object is considered to be unreliable. Hereby an accurate representation of shape and location of a remotely located optical shape sensing fiber is possible.

The optical shape sensing elements preferably comprise Rayleigh sensors, or Fiber Bragg Gratings, such as known by the skilled person. The optical console and method for optical interrogation of the optical shape sensing elements may be performed in several ways, such as known by the skilled person.

In a preferred embodiment, the optical shape sensing system is arranged to generate a three-dimensional image of parts of both of the first and second optical fibers with one common three-dimensional coordinate system. Thus, with the system according to the invention, it is possible to visualize one long sensed 3D shape, without severe shape and position inconsistencies, even though two or even more optical fibers cooperate to produce the shape sensing data to the complete image.

In a second aspect, the invention provides a device comprising an optical shape sensing system comprising according to the first aspect. Especially, the device may be a medical device or a robot. However, it is understood that in general, the invention is applicable to systems for tracking, navigation and shape reconstruction. The first and second optical fibers may be arranged to sense an elongated part of the device, e.g. built into, embedded within, or attached outside such elongated part of the device, e.g. an elongated interventional part of a medical instrument.

In a third aspect, the invention provides a method for increasing an effective length of an optical shape sensing system, as defined by appended claim 15.

It is appreciated that the same advantages and embodiments of the first aspect apply as well for the second and third aspect. In general the first, second, and third aspects may be combined and coupled in any way possible within the scope of the invention. These and other aspects, features and/or advantages of the invention will be apparent from and elucidated with reference to the embodiments described hereinafter.

BRIEF DESCRIPTION OF THE DRAWINGS

Embodiments of the invention will be described, by way of example only, with reference to the drawings, in which.

DESCRIPTION OF EMBODIMENTS

Figure 1:
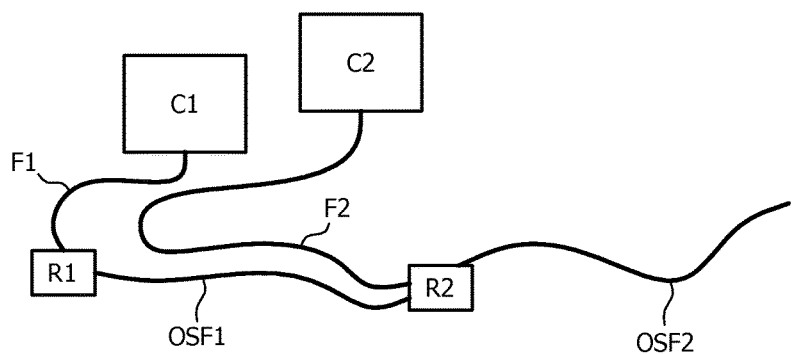
FIG. 1 illustrates a block diagram of one embodiment.

FIG. 1 illustrates an optical shape sensing (OSS) embodiment with an optical console system with two separate optical consoles C1, C2 each with respective optical fibers OSF1, OSF2 connected thereto, both of these OSF1, OSF2 have optical shape sensing elements. Each optical fiber OSF1, OSF2 has a limited shape sensing length. In this embodiment, one reference point in space R1, i.e. a proximal end of the first optical fiber OSF1, can be selected as reference point for one common coordinate system to be used in a processor as a common frame of reference (not shown for simplicity). The point R1 can be defined as origin in the coordinate system, and the 3D coordinate system can be defined also based on the orientation of the first optical fiber OSF1 also in this point R1, or based on an orientation determined on the basis of a short length of the first optical fiber OSF1 in the vicinity of point R1. The distal end point R2 of the first optical fiber OSF1 is selected to be spatially common to a proximal point of the second optical fiber OSF2. By registering R2 as a starting point for the shape sensing of the second optical fiber OSF2, it is now possible to only accurately track shape over the length possible for one fiber (1.5-2 meters), but for the double length, i.e. up to 4 meters, and this principle can be repeated several times, so the total length can be increased even more.

It is to be understood that the optical fiber parts F1, F2 interconnecting the optical fiber parts used for shape sensing OSF1, OSF2 with the optical consoles C1, C2 are not used for shape sensing. These parts F1, F2 can be separate optical fibers optically connected to separate optical shape sensing fibers OSF1, OSF2, but they can also form part of long optical shape sensing fibers of which only distal parts OSF1, OSF2 are used for shape sensing.

Figure 2:
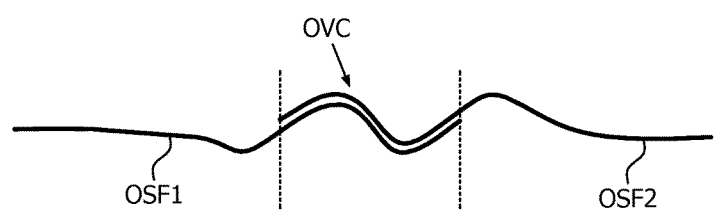
FIG. 2 illustrates another embodiment with two optical fibers with an overlapping curve.

FIG. 2 illustrates two optical fibers OSF1, OSF2 with optical sensing elements. The two optical fibers OSF1, OSF2 are placed with an overlapping curve OVC or region, i.e. a distal end of a first optical fiber OSF1 is arranged spatially adjacent to a proximal end of a second optical fiber OSF2. The overlapping curve OVC or region is indicated by the dashed lines. This can be obtained by mechanically fixing the two optical fibers OSF1, OSF2 closely together, e.g. within one elongated part of a medical device. By registering spatial points of the distal curve of the first optical fiber OSF1 to the proximal curve of the second optical fiber OSF2, the shape of the second optical fiber OSF2 can be treated as a shape in the coordinate system, or frame of reference, defined by the first optical fiber OSF1, thus it is possible to add the proximal points of the second optical fiber OSF2 to its own points transformed to the frame of reference, or coordinate system, of the first optical fiber OSF1, effectively increasing the length of the shape sensed device. The two optical fibers OSF1, OSF2 can be part of the same medical device. For simplicity, the processor registering the position data in relation to one common coordinate system is not shown, and neither is the optical console system arranged for optically interrogating the two optical fibers OSF1, OSF2 to preferably be able to generate one 3D image visualizing the continuous 3D shape of the total length of the shape sense device.

A method to register two curve shapes using mutual curve OVC information can be done in different ways. A preferred method comprises identifying a stable curvature in a reconstructed image of a shape of the first optical fiber OSF1, and matching the stable curvature to a curvature from a reconstructed image of a shape of the second optical fiber OSF2, and aligning the matched curvatures. E.g. the stable curvature and the curvature can be matched by comparing bend radii, by comparing gradients of coordinates in the curvature. Especially, the step of identifying a stable curve may comprise 1) measuring the radius of at least one bend in the curve of the reconstructed image of a shape sensing fiber equipped instrument, 2) comparing a bend radius from a subsequent reconstructed image with the prior reconstructed image of the first optical sensor OSF1, 3) determining whether the bend radii meet a predefined matching criteria, and 4) saving the radius and location of the bend if the matching criteria is met.

Figure 3:
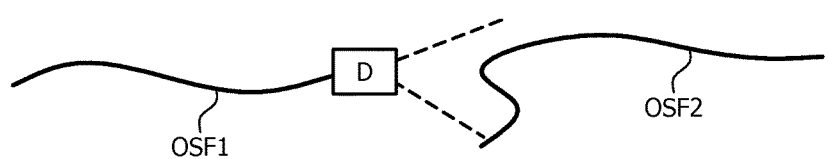
FIG. 3 illustrates an embodiment with a detector attached to a distal part of the first optical fiber in order to register a position of the second optical fiber, FIG. 4 example of a hierarchical structure for data registration for 5 objects with redundant registration information for two objects.

FIG. 3 illustrates a sketch of an embodiment where an image detector is attached to a part of a first optical shape sensing fiber OSF1, preferably it is attached to a distal part of the first optical shape sensing fiber OSF1. This detector is used to provide an image of a second optical shape sensing fiber OSF2, so as to be able to identify at least one point in space of this second optical shape sensing fiber OSF2. In principle, the second optical shape sensing fiber OSF2 may belong to a separate OSS device, but if it is possible to detect a point in space, e.g. of its proximal end, it can be registered in relation to a coordinate system defined by the first optical shape sensing fiber OSF1. Depending on the technology used, e.g. X-ray, (visual light) camera, ultrasound, radio frequency technique, a distance between the imaging device and the second optical shape sensing fiber OSF2 can be a few centimeters up to many meters.

By adding a tracking technology, such as electromagnetic sensors, optical markers, accelerometers etc. the location and orientation of an OSS tracked device can be known in reference to other OSS enabled devices.

Figure 4:
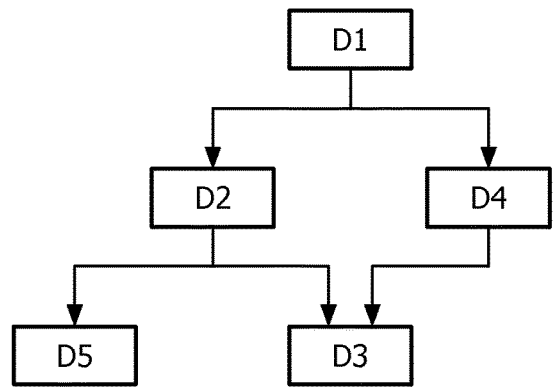

FIG. 4 illustrates an example of a hierarchical data structure with position and orientation data registrations for five devices D1, D2, D3, D4, D5 of which all or only some include optical shape sensing capabilities. By repeating the above steps of concatenating OSS devices, adding a new object or device to the distal part of a previous device, a hierarchical data structure, i.e. a tree or chain, of registrations (illustrated by arrows) can be made, where each device's position and orientation is known in its parent's coordinate system, and therefore in the parent's parent's coordinate system etc. A registration chain is a simplified tree where each device only has one child registration. As seen, redundant registration data exist for devices D3 and D4. Determination of position of device D3 can be based either on data from D1 and D2 or from D1 and D4.

The solution can use intermediate registrations not based on shape sensing as well, e.g. if a device is registered to a table and the frame of reference of the table with respect to an imaging device is known and this imaging device is used to track an OSS enabled device, any further devices registered to the tracked OSS enabled devices are known in the frame of reference of the original OSS device.

It is further possible to utilize registration redundancy for error correction and accuracy improvement in shape sensing. A potential issue with this approach of combining several OSS devices is that the accuracy of each device further down the registration tree degrades with the shape reconstruction and the registration accuracies. By introducing connections from a device higher up in the tree hierarchy to a single device further down the accuracy of a single registration can be assessed:

In case a shape reconstruction failed, it can be ignored and the correct shape can be used.

This can also be used to improve the outlier rejection algorithm by adaptive modification of thresholds.

If it is known one shape and/or registration is more accurate (by using internal metrics) the better shape and/or registration can be used This can also be used to correct the incorrect or less accurate shape. For instance, if the shape reconstruction is less accurate for the first tether (since error increases with length), the shape from the overlapping region of the proximal portion of the second OSS enabled device can be used to improve the former's shape.

If the better one is not known, an average or weighted average can be taken.

Due to the principles involved in OSS, error is integrated and accumulates along the length of an optical fiber. It is also known that fiber accuracy can be increased by increasing the thickness of the fiber. As a result, for applications where accuracy is extremely critical, such as neural procedures, shorter and potentially thicker fibers can be used instead of less accurate longer fibers. These shorter fibers are stitched together using the steps described in the document in order to achieve a longer length and still have higher accuracy.

Figure 5:
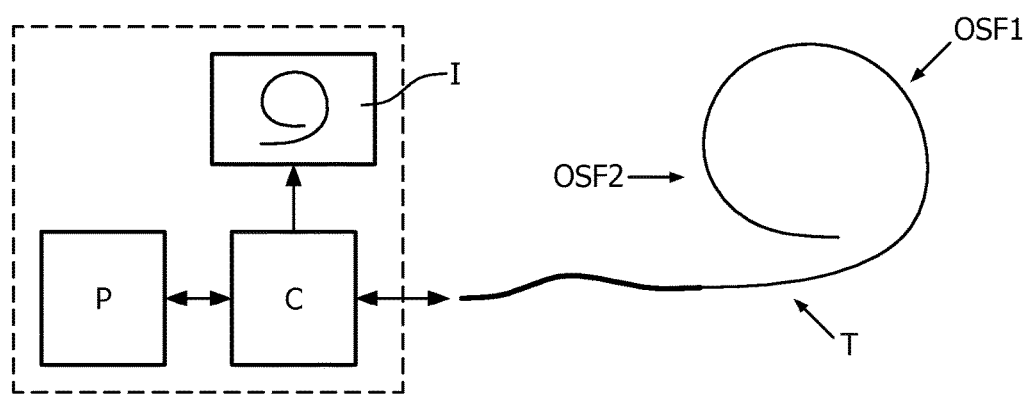
FIG. 5 illustrates a block diagram of a medical device embodiment with two optical fibers cooperating to provide shape sensing of one long tether.
Figure 6:
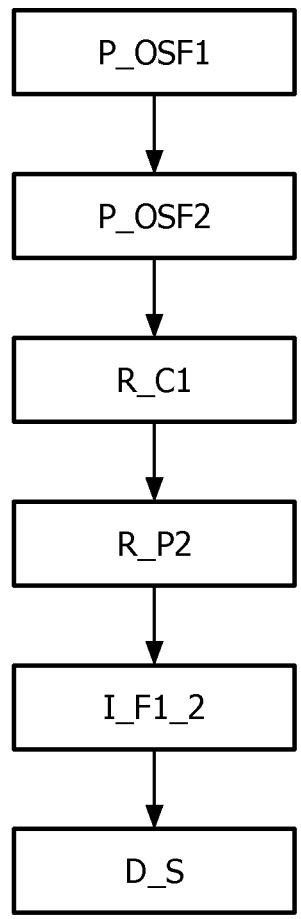
FIG. 6 illustrates steps of a method embodiment.

FIG. 5 illustrates an example of a medical application of the invention, namely a medical device with a tether T with a distal part in which two optical shape sensing fibers OSF1, OSF2 are arranged and combined according to this invention to provide an increased optical shape sensing length of the tether T, e.g. using the overlapping curve principle as show in FIG. 2. The two fibers OSF1, OSF2 can be arranged within a lumen of the tether, be attached to an outer surface of the tether, or in other ways follow the shape of the elongated tether T. The two sensing fibers OFS1, OSF2 are connected to an optical console C arranged to optically interrogate the two fibers OSF1, OSF2. A processor P serves to register position data for both optical fibers OSF1, OSF2 in one common coordinate system based on the first fiber OSF1 arranged proximal to the portion of the tether T being shape sensed. The processor P and optical console C cooperate to generate an image I showing a 3D shape of the total shape sensed part of the tether T as one continuous curve.

The invention is also advantageous in a number of other applications, where significantly longer lengths of OSS can be used. An example is in robotic applications as well as for tracking the motion of the C-arm or the bending of a table. Another instance could be tracking the arm of a robotic device using one OSS device and having multiple branch off from the distal portion of the first device, and the transformation (in all 6 degrees, including roll about its own axis) is known between the links of the robot.

To sum up, the invention provides an optical shape sensing system and method with at least two optical fibers OSF1, OSF2 both comprising optical shape sensing elements. A processor P is arranged to register a coordinate system indicative of a position of one of the optical fibers OSF1 in space, and to register a position R2 of the other optical fiber OSF2 in relation to this coordinate system. An optical console system C, C1, C2 serves to interrogate the optical shape sensing elements in both optical fibers OSF1, OSF2, and to accordingly determine a measure of a three-dimensional shape I of both optical fibers OSF1, OSF2, based on the registered position R2 of the second optical fiber OSF2 in relation to the coordinate system. This provide the possibility of providing 3D optical shape sensing of the length of both optical fibers OSF1, OSF2, thus allowing 3D shape reconstruction of e.g. long medical devices with lengths of several meters. More than two shape sensing optical fibers, e.g. incorporated in separate devices, can be registered in this manner in a hierarchical data structure, thus allowing shape sensing of very long instruments.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An optical shape sensing system comprising
   a first optical fiber (OSF1) comprising optical shape sensing elements,
   a second optical fiber (OSF2) comprising optical shape sensing elements,
   a processor (P) arranged to register a first coordinate system indicative of a position of the first optical fiber (OSF1) in space, and to register a position (R2) of the second optical fiber (OSF2) in relation to the first coordinate system, and
   an optical console system (C, C1, C2) arranged for interrogating the optical shape sensing elements in both of the first and second optical fibers (OSF1, OSF2), and to accordingly determine a measure of a three-dimensional shape (I) of at least parts of both of the first and second optical fibers (OSF1, OSF2), based on the registered position (R2) of the second optical fiber (OSF2) in relation to the first coordinate system,
   characterized in that
   the first optical fiber (OSF1) and the second optical fiber (OSF2) are mechanically concatenated so that the second optical fiber (OSF2) serves to extend an effective length of the first optical fiber (OSF1) or to improve accuracy of a three-dimensional shape reconstruction of the first optical fiber (OSF1), and
   the processor (P) is arranged to register a position in space (R2) and an orientation of a proximal part of the second optical fiber (OSF2) in relation to the first coordinate system.

2. Optical shape sensing system according to claim 1, wherein the optical console system comprises a first optical console (C1) arranged for interrogating the optical shape sensing elements in the first optical fiber (OSF1), and a second optical console (C2) arranged for interrogating the optical shape sensing elements in the second optical fiber (OSF2).

3. Optical shape sensing system according to claim 1, wherein an image detector (D) is arranged at or near a distal part of the first optical fiber (OSF1), and wherein the image detector (D) is arranged to detect a measure of the position of the second optical fiber (OFS2).

4. Optical shape sensing system according to claim 3, wherein the image detector (D) comprises at least one of: a visible light camera, an ultrasound sensor, a radio frequency sensor, and an x-ray device.

5. Optical shape sensing system according to claim 1, wherein a distal part of the first optical fiber (OSF1) is mechanically arranged adjacent to the proximal part of the second optical fiber (OSF2), so as to form an overlapping curve (OVC) between the first and second optical fibers (OSF1, OSF2), and wherein the optical console system (C, C1, C2) is arranged to generate a measure of three-dimensional shape of at least part of said overlapping curve (OVC) between the first and second optical fibers (OSF1, OSF2).

6. Optical shape sensing system according to claim 5, arranged to correct a three-dimensional shape reconstruction of the first optical fiber (OSF1) in response to the measure of three-dimensional shape of said at least part of said overlapping curve (OVC) between the first and second optical fibers (OSF1, OSF2).

7. Optical shape sensing system according to claim 1, comprising an auxiliary object (D3, D4, D5), and wherein the processor (P) is arranged to register a position of the auxiliary object in relation to the first coordinate system in a hierarchical data structure.

8. Optical shape sensing system according to claim 7, comprising a plurality of auxiliary objects (D3, D4, D5), wherein the processor (P) is arranged to register position of the plurality of auxiliary objects (D3, D4, D5) in relation to the first coordinate system in a hierarchical data structure, wherein at least one of the plurality of objects (D3) is linked to position data registered for at least two objects (D2, D4) higher up in the hierarchical data structure.

9. Optical shape sensing system according to claim 7, wherein at least one of the plurality of auxiliary object comprises a third optical fiber (D3) with optical shape sensing elements, and wherein the optical shape sensing system is arranged to correct a three-dimensional shape reconstruction of the third optical fiber (D3) in response to data registered higher up in the hierarchical data structure than where position data for the third optical fiber (D3) is registered.

10. Optical shape sensing system according to claim 1, wherein the optical shape sensing elements comprise at least one of: Rayleigh sensors, and fiber Bragg gratings.

11. Optical shape sensing system according to claim 1, arranged to generate a three-dimensional image (I) of parts of both of the first and second optical fibers (OSF1, OSF2) with one common three-dimensional coordinate system.

12. Method for increasing an effective length of an optical shape sensing system, the method comprising
providing (P_OSF1) a first optical fiber comprising optical shape sensing elements,
providing (P_OSF2) a second optical fiber comprising optical shape sensing elements,
registering (R_C1) a first coordinate system indicative of a position of the first optical fiber in space,
registering (R_P2) a position of the second optical fiber in relation to the first coordinate system,
interrogating (I_F1_2) the optical shape sensing elements in both of the first and second optical fibers, and
determining (D_S) a measure of a three-dimensional shape of at least parts of both of the first and second optical fibers, based on the registered position of the second optical fiber in relation to the first coordinate system,
characterized in that
the method comprises concatenating the first optical fiber (OSF1) and the second optical fiber (OSF2) to extend an effective length of the first optical fiber (OSF1) and
registering a position in space (R2) and an orientation of a proximal part of the second optical fiber (OSF2) in relation to the first coordinate system.

* * * * *